United States Patent
Lee et al.

(10) Patent No.: US 10,633,768 B2
(45) Date of Patent: Apr. 28, 2020

(54) FUNCTIONAL COPPER SULFIDE COMPOSITION AND A FUNCTIONAL FIBER PRODUCED THEREFROM

(71) Applicant: RETEND CO., LTD., Gunpo-si (KR)

(72) Inventors: Bong Hee Lee, Anyang-si (KR); Kyu Sang Lee, Anyang-si (KR)

(73) Assignee: TEMPUP CO., LTD, Gunpo-si (KR)

( * ) Notice: Subject to any disclaimer, the term of this patent is extended or adjusted under 35 U.S.C. 154(b) by 158 days.

(21) Appl. No.: 15/561,485

(22) PCT Filed: Mar. 22, 2016

(86) PCT No.: PCT/KR2016/002885
§ 371 (c)(1),
(2) Date: Sep. 25, 2017

(87) PCT Pub. No.: WO2016/159556
PCT Pub. Date: Oct. 6, 2016

(65) Prior Publication Data
US 2018/0066384 A1    Mar. 8, 2018

(30) Foreign Application Priority Data
Mar. 27, 2015   (KR) .................... 10-2015-0043117

(51) Int. Cl.
| | | |
|---|---|---|
| *D01F 1/10* | (2006.01) | |
| *D01F 1/09* | (2006.01) | |
| *D06M 11/53* | (2006.01) | |
| *D06M 11/56* | (2006.01) | |
| *D06M 11/83* | (2006.01) | |
| *C01G 3/05* | (2006.01) | |
| *C01G 3/10* | (2006.01) | |
| *C01G 3/12* | (2006.01) | |
| *D06M 13/332* | (2006.01) | |
| *C07C 211/09* | (2006.01) | |
| *C07C 211/13* | (2006.01) | |
| *G01N 21/3581* | (2014.01) | |

(52) U.S. Cl.
CPC ............... *D01F 1/10* (2013.01); *C01G 3/05* (2013.01); *C01G 3/10* (2013.01); *C01G 3/12* (2013.01); *C07C 211/09* (2013.01); *C07C 211/13* (2013.01); *D01F 1/09* (2013.01); *D06M 11/53* (2013.01); *D06M 11/56* (2013.01); *D06M 13/332* (2013.01); *G01N 21/3581* (2013.01)

(58) Field of Classification Search
None
See application file for complete search history.

(56) References Cited

U.S. PATENT DOCUMENTS

| | | | |
|---|---|---|---|
| 4,336,028 A | 6/1982 | Tomibe et al. | |
| 4,378,226 A | 3/1983 | Tomibe et al. | |
| 4,784,910 A * | 11/1988 | Nagai | H01B 1/122 427/126.1 |
| 5,144,913 A * | 9/1992 | Yasui | A01K 27/006 119/850 |
| 5,269,973 A * | 12/1993 | Takahashi | D06M 11/53 252/519.33 |
| 5,424,116 A * | 6/1995 | Takahashi | C08J 7/12 427/121 |
| 5,431,856 A * | 7/1995 | Okoniewski | D06M 10/025 252/500 |
| 6,228,922 B1 * | 5/2001 | Wang | C08K 3/08 524/413 |
| 2014/0154482 A1 * | 6/2014 | Jang | F41H 3/00 428/196 |

FOREIGN PATENT DOCUMENTS

| | | |
|---|---|---|
| KR | 1019840002108 A | 9/1983 |
| KR | 1020120115031 A | 10/2012 |
| KR | 1020130007726 A | 1/2013 |
| KR | 1020130099474 A | 9/2013 |

OTHER PUBLICATIONS

English translation of KR-2013-0099474, Sep. 2013; 20 pages.*
English translation of KR-2012-0115031, Oct. 2012; 15 pages.*
International Search Report of PCT/KR2016/002885, dated Jul. 29, 2016, English Translation.

* cited by examiner

*Primary Examiner* — Helene Klemanski
(74) *Attorney, Agent, or Firm* — STIP Law Group, LLC

(57) ABSTRACT

The present invention relates to a functional copper sulfide composition and a functional fiber prepared therefrom, and more particularly, a functional copper sulfide composition comprising a copper salt, a metal salt, a reducing agent, a sulfur compound, a catalyst, a poly amine, an alkali compound and a pH adjusting agent; and a functional fiber prepared by treating the composition with a fiber.

4 Claims, No Drawings

FUNCTIONAL COPPER SULFIDE COMPOSITION AND A FUNCTIONAL FIBER PRODUCED THEREFROM

CROSS-REFERENCE TO RELATED APPLICATIONS

This application is the U.S. National Phase under 35 U.S.C. § 371 of International Application No. PCT/KR2016/002885 filed on Mar. 22, 2016, which in turn claims the benefit of Korean Application No. 10-2015-0043117, filed on Mar. 27, 2015, the disclosures of which are incorporated by reference into the present application.

TECHNICAL FIELD

The present invention relates to a functional copper sulfide composition and a functional fiber prepared therefrom, and more particularly, a functional copper sulfide composition comprising a copper salt, a metal salt, a reducing agent, a sulfur compound, a catalyst, a polyvalent amine, an alkali compound and a pH adjusting agent; and a functional fiber prepared by treating the composition with a fiber.

BACKGROUND ART

Most synthetic fibers and natural fibers have a static electricity due to friction between fibers or between fiber and skin. The static electricity causes various problems such as fire, skin trouble, discomfort, etc. not only in daily life but also in industrial field.

In order to solve the problem of static electricity generation in the fiber, the fiber is treated with an antistatic agent, and the various methods for imparting conductivity to fibers have been developed.

A method of treating fibers using an antistatic agent is inexpensive and simple in process, but there is a disadvantage that the antistatic effect is significantly reduced during washing and long-term use.

As a method for imparting conductivity to fibers, there are a method of mixing carbon black or metal powder having conductivity with a polymer, and then spinning it to give a fiber; a method of plating metal on the surface of a fiber; a method of depositing a metal powder in a hole existing on the surface of a fiber, and the like.

A method for producing a conductive fiber by mixing carbon black or a metal powder with a polymer cannot form uniform mixture of carbon black or metal powder and the polymer, and the strength, elongation and thermal properties of the fiber are significantly deteriorated during the spinning.

An electroless plating method is widely used as a method of plating a metal on a fiber surface. In the electroless plating method, in order to improve the adhesion between the fiber and the metal film, a process of forming wrinkles on the surface, a cleaning process using strong acid, and the like are necessary. Therefore, the fiber processing process is very complicated, and it is difficult to expect the inherent physical properties of the produced conductive fibers.

In method of depositing the metal powder in the pores present on the fiber surface, the fiber has to include pores larger than the particles of metal. Therefore, porous fibers with large diameter pores should be prepared during fiber production. A unique spinning process is required to fabricate the porous fibers. And the mechanical, chemical and thermal properties of the fibers are significantly degraded.

In order to solve the above problems, various techniques for producing conductive fibers have been developed by forming metal compound on the surface of a fiber.

U.S. Pat. No. 4,336,028 discloses a method for producing a conductive fiber by treating a composition comprising a divalent copper ion, a reducing agent and sulfur-containing compound with the acrylic fiber, wherein a reducing agent reduces divalent copper ion into monovalent copper ion and sulfur-containing compound forms copper sulfide by reacting with monovalent copper ion.

U.S. Pat. No. 4,378,776 discloses a process for preparing a conductive fiber coated with copper sulfide by treating a composition comprising copper compounds, reducing agents, sulfur compounds and pH adjusting agents with fiber.

Also, Korean Patent No. 10-1984-0002108 discloses a conductive fiber manufactured by treating at least one kind of fiber selected from a polyamide-fibers, polyester fibers, rayon fibers, copper ammonium fibers, animal fibers and vegetable fibers with composition comprising a divalent copper ion, a reducing agent capable of reducing divalent copper ions to monovalent copper ions, and a compound capable of releasing at least one sulfur component.

However, the above documents disclose that copper sulfide is coordinated to fibers to impart conductivity. The color of the fiber changes drastically because copper sulfide is desorbed during repeated washing or prolonged use. And washing resistance, durability, moisture resistance, alkali resistance, and the like are sharply reduced.

In addition, the conductive fibers cannot be widely used in the fields of apparel, industrial and military field because antibacterial, deodorant, far-infrared radiation, wound healing, heat storage and insulation, electromagnetic shielding, and static electricity property are inferior.

DISCLOSURE

Technical Problem

The present invention has been made to solve the above problems of the prior art, and an object of the present invention is to provide a functional copper sulfide composition with excellent conductivity, washing resistance, washability, durability, moisture resistance and alkali resistance, wherein the color of the fiber is maintained even when it is washed repeatedly or used for a long time.

In addition, the present invention is to provide a functional fiber which has excellent an antibacterial, deodorant, far-infrared radiation, wound healing, skin aging prevention, heat storage and insulation, electromagnetic shielding and static electricity removal characteristics, and can be widely used in clothing, industrial and military field.

Technical Solution

In order to achieve the above object, the present invention provides a functional copper sulfide composition comprising a copper salt, a metal salt, a reducing agent, a sulfur compound, a catalyst, a polyhydric amine, an alkali compound and a pH adjusting agent.

In one embodiment of the present invention, the composition comprises 10 to 40% by weight of a copper salt, 1 to 10% by weight of a metal salt, 5 to 30% by weight of a reducing agent, 5 to 30% by weight of a sulfur compound, 1 to 5% by weight of a catalyst, 1 to 10% by weight of a polyhydric amine, 1 to 10% by weight of an alkali compound and 1 to 5% by weight of a pH adjusting agent.

In one embodiment of the present invention, the copper salt is one or more selected from the group consisting of cupric sulfate salt, cupric chloride salt, cupric nitrate salt, cupric acetate salt and cupric sulfate ammonium salt; the metal salt is an inorganic acid salt or an organic acid salt of a metal selected from the group consisting of gold, silver, platinum, nickel, manganese, cobalt, chromium, zinc, palladium, rhodium, ruthenium, osmium, magnesium, iron and iridium; and the reducing agent is one or more selected from the group consisting of metal copper, hydroxylamine, ferrous sulfate, ammonium vanadate, furfural, sodium hypophosphate, sodium hypophosphite, sodium hydrogen sulfite, glucose and phenyl compounds; the sulfur compound is one or more selected from sodium sulfide, sulfur dioxide, sulfurous acid, sodium sulfite, sodium hydrogen sulfite, sodium pyrosulfite, hyposulfurous acid, sodium hydrosulfite, sodium thiosulfate, potassium thiosulfate, ammonium thiosulfate, thiourea dioxide, hydrogen sulfide, formaldehyde sodium sulfoxylate; the catalyst is one or more selected from the group consisting of magnesium chloride, potassium chloride, calcium chloride, zinc acetate, ammonium chloride, ammonium sulfate, ammonium carbonate and ammonium nitrate; the polyhydric amine is one or more selected from the group consisting of methylene diamine, ethylene diamine, trimethylene diamine, tetramethylene diamine, pentamethylene diamine, hexamethylenediamine, heptamethylenediamine, diethylene triamine, triethylene tetramine, tetraethylene pentamine and pentaethylene hexamine; the alkali compound is one or more selected from sodium hydroxide, potassium hydroxide, sodium carbonate, potassium carbonate, sodium hydrogen carbonate and potassium hydrogen carbonate; and the pH adjusting agent is at least one selected from sulfuric acid, hydrochloric acid, phosphoric acid, nitric acid, citric acid, acetic acid and salts thereof.

The present invention also relates to a functional fiber which is produced by treating one or more fibers selected from a plant fiber, an animal fiber, a synthetic fiber and a recycle fiber with the functional copper sulfide composition, wherein the surface of the fiber is coated with at least one functional group selected from a thiol group, thiocarbonyl group, thiourea group, azol group, an amino group, a cyano group and an amide group, a copper sulfide and a metal sulfide are coordinately bonded to the functional group, the functional group is 1 to 10% by weight based on the total fiber weight, the copper sulfide is 1 to 15% by weight based on the total fiber weight, and the metal sulfide is 0.1 to 5% by weight based on the total fiber weight.

In one embodiment of the present invention, the functional fiber has the far-infrared emissivity of 0.895% or more at 37° C. and 5 to 20 μm, the far-infrared radiation energy of $3.45 \times 10^2$ W/m$^2$·μm or more, the far-infrared emissivity after 40 times of washing of 0.892% or more, and the far-infrared radiation energy of $3.41 \times 10^2$ W/m$^2$·μm or more.

In one embodiment of the present invention, the functional fiber has at least one function selected from the group consisting of antibacterial, deodorant, far-infrared radiation, wound healing, skin aging prevention, thermal storage and thermal insulation, electromagnetic shielding and static elimination.

In addition, the present invention provides a molded article comprising the functional fiber, wherein the molded article includes clothing, socks, gloves, bands, abdominal binder, masks, hats, bandage, scarf, bedclothes, burn pad, a hospital gown, or an industrial filter.

Advantageous Effects

The present invention can provide a functional fiber with excellent conductivity, washing resistance, washability, durability, moisture resistance and alkali resistance, wherein the color of the fiber is maintained even when it is washed repeatedly or used for a long time.

In addition, the present invention can provide a functional fiber which has excellent an antibacterial, deodorant, far-infrared radiation, wound healing, skin aging prevention, thermal storage and thermal insulation, electromagnetic shielding and static electricity removal characteristics, and can be widely used in industrial and military field such as clothing, socks, gloves, bands, abdominal binder, masks, hats, bandage, scarf, bedclothes, burn pad, a hospital gown, an industrial filter or filler.

BEST MODE

Hereinafter, the present invention will be described in detail based on examples. The term and example in the present invention is used to describe the invention more specifically and the scope of the present invention is not limited thereto.

Technical terms and scientific terms used in the present invention, unless otherwise defined, indicates the meaning well known to those of ordinary skill in the art.

The present invention relates to a functional copper sulfide composition comprising a copper salt, a metal salt, a reducing agent, a sulfur compound, a catalyst, a polyhydric amine, an alkali compound and a pH adjusting agent.

The composition may comprises 10 to 40% by weight of a copper salt, 1 to 10% by weight of a metal salt, 5 to 30% by weight of a reducing agent, 5 to 30% by weight of a sulfur compound, 1 to 5% by weight of a catalyst, 1 to 10% by weight of a polyhydric amine, 1 to 10% by weight of an alkali compound and 1 to 5% by weight of a pH adjusting agent.

The copper salt is used to form a divalent copper ion, and the formed divalent copper ions are reduced to monovalent copper ion by a reducing agent and coordinate with the functional group on the surface of fibers.

The copper salt is one or more selected from the group consisting of cupric sulfate salt, cupric chloride salt, cupric nitrate salt, cupric acetate salt and cupric sulfate ammonium salt.

The copper salt is used in an amount of 10 to 40% by weight based on the total weight of composition. When the content is less than 10% by weight, the content of copper sulfide introduced into the fibers is insufficient, so that the conductivity, the far-infrared ray emissivity, etc. of fibers decrease. When it exceeds 40% by weight, the conductivity of fiber is increased, but the physical properties of fiber may be reduced and a large amount of copper sulfide precipitate may be formed.

The metal salt can be used to improve various purposes such as washability, washing resistance, moisture resistance, alkali resistance and durability.

The metal salt can be selected among an inorganic acid salt or an organic acid salt of a metal selected from the group consisting of gold, silver, platinum, nickel, manganese, cobalt, chromium, zinc, palladium, rhodium, ruthenium, osmium, magnesium, iron and iridium. Preferred examples include silver sulfate, nitrate, palladium chloride, nickel sulfate, and zinc sulfate.

The metal ion formed from the metal salt forms a metal sulfide by reaction with a sulfur compound, and can form coordinate bond with a functional group existing on the surface of the fiber. In addition, the metal ions combine with sulfur atoms of copper sulfide formed on the surface of fiber to form a complex.

The content of the metal salt is preferably 1 to 10 wt %. When the content is less than 1% by weight, the washability, washing resistance and durability of fibers decrease. When it exceeds 10% by weight, the conductivity of fiber is rather reduced.

The reducing agent is used to reduce the divalent copper ion formed from copper salt into monovalent copper ion.

The reducing agent is one or more selected from the group consisting of metal copper, hydroxylamine, ferrous sulfate, ammonium vanadate, furfural, sodium hypophosphate, sodium hypophosphite, sodium hydrogen sulfite, glucose and phenyl compounds.

The content of the reducing agent is preferably 5 to 30% by weight, and when the content is less than 5% by weight, divalent copper ions cannot be effectively reduced to monovalent copper ions. When it exceeds 30% by weight, the excess monovalent copper ion is changed to divalent copper ion or metal copper, so that a copper oxide or a metal copper precipitate is formed on the surface of the fiber and the physical properties of fiber are decreased.

The sulfur compound is used to form copper sulfide or metal sulfide by reaction with copper ion from copper salt or metal ion from metal salt.

The sulfur compound is one or more selected from sodium sulfide, sulfur dioxide, sulfurous acid, sodium sulfite, sodium hydrogen sulfite, sodium pyrosulfite, hyposulfurous acid, sodium hydrosulfite, sodium thiosulfate, potassium thiosulfate, ammonium thiosulfate, thiourea dioxide, hydrogen sulfide, formaldehyde sodium sulfoxylate.

The content of the sulfur compound is preferably 5 to 30 wt %, and when the content is less than 5% by weight, it is impossible to efficiently form copper sulfide or metal sulfide and it is difficult to develop conductivity, far-infrared emissivity, durability and washability. When it exceeds 30% by weight, the stability of the composition cannot be ensured and a uniform coating of copper sulfide cannot be formed on the surface of fiber.

The catalyst is used to form uniformly the copper sulfide on the surface of fiber by regulating the rate of formation of copper sulfide. When copper sulfide is produced at a high rate, a powdery precipitate is formed, and there arises a problem that copper sulfide cannot be uniformly adsorbed on the surface of fiber. The sulfur ion is slowly produced from the sulfur compounds by use of catalyst, and the generation rate of copper sulfide can be controlled. That is, copper ions existing on the surface of the fiber are slowly combined with sulfur ions and the copper sulfide produced can be uniformly bonded to the surface of fiber.

The catalyst is one or more selected from the group consisting of magnesium chloride, potassium chloride, calcium chloride, zinc acetate, ammonium chloride, ammonium sulfate, ammonium carbonate and ammonium nitrate.

The content of the catalyst is preferably 1 to 5 wt %, and when the content is less than 1 wt %, the production rate of copper sulfide cannot be controlled. When exceeds 5% by weight, the stability of composition is lowered, a powdery precipitate is formed, and non-uniform adsorption of copper sulfide occurs.

The polyvalent amine forms a complex with the divalent copper ion, so that copper oxide or metallic copper precipitate, which is byproduct formed on the fiber surface, decreases and copper sulfide can be uniformly adsorbed on surface of fiber.

The monovalent copper ions reduced by the reducing agent form a coordination bond with a functional group of fiber, but the monovalent copper ions, which do not bind with a functional group, change to metal copper or copper ion. The metal copper precipitate adheres to the surface of the fiber and the reaction vessel, so that it adversely affects the physical properties of the fiber and lowers the workability by releasing $SO_2$, NO, and the like through reaction with the sulfuric acid, nitric acid, and the like used as pH controller. The divalent copper ion is converted into copper oxide to form an oxide film on the surface of the fiber, and deteriorates the properties of the fiber by preventing the bonding of copper sulfide.

The polyvalent amine forms a complex with a divalent copper ion, so that it is possible to prevent a divalent copper ion from being changed into the copper oxide, and the amount of copper oxide produced can be reduced dramatically.

The polyhydric amine is one or more selected from the group consisting of methylene diamine, ethylene diamine, trimethylene diamine, tetramethylene diamine, pentamethylene diamine, hexamethylenediamine, heptamethylenediamine, diethylene triamine, triethylene tetramine, tetraethylene pentamine and pentaethylene hexamine.

The content of the polyvalent amine is preferably 1 to 10% by weight, and when the content is less than 1% by weight, the polyvalent amine cannot form a sufficient complex with the divalent copper ion. When it exceeds 10% by weight, the content of copper sulfide present on the surface of the fiber is reduced, and the conductivity, washing resistance, durability, and the like cannot be improved.

The alkali compound loosens the structure of the fiber molecule, promotes the coordination bond of the functional groups of fiber and the copper sulfide, and forms efficiently copper sulfide on the surface of fiber.

The alkali compound is one or more selected from sodium hydroxide, potassium hydroxide, sodium carbonate, potassium carbonate, sodium hydrogen carbonate and potassium hydrogen carbonate.

The content of the alkali compound is preferably 1 to 10 wt %, and when the content less than 1% by weight, the effect is insignificant. If it exceeds 10% by weight, the fiber surface is damaged and properties such as conductivity, washing resistance and durability cannot be exhibited.

The pH adjusting agent is required to ensure the stability of the composition and to control the rate of formation of copper sulfide. The pH adjusting agent is at least one selected from sulfuric acid, hydrochloric acid, phosphoric acid, nitric acid, citric acid, acetic acid and salts thereof.

The content of the pH adjusting agent is preferably 1 to 5% by weight, and when the content is less than 1% by weight, the effect is insignificant. If it exceeds 5% by weight, the stability of the composition deteriorates and a powdery precipitate is formed or non-uniform adsorption of copper sulfide occurs.

The present invention relates to a method for producing the functional fiber comprising the step for preparing a functional copper sulfide composition, which comprises 10 to 40% by weight of a copper salt, 1 to 10% by weight of a metal salt, 5 to 30% by weight of a reducing agent, 5 to 30% by weight of a sulfur compound, 1 to 5% by weight of a catalyst, 1 to 10% by weight of a polyhydric amine, 1 to 10% by weight of an alkali compound and 1 to 5% by weight of a pH adjusting agent; the step for introducing functional groups selected from a thiol group, thiocarbonyl group, thiourea group, an azole group, an amino group, a cyano group and an amide group to one or more fiber selected from vegetable fibers, animal fibers, synthetic fibers and regenerated fibers; the step for coordinating copper sulfide on the surface of fiber by treating the surface treated fibers with the above composition; and the step for washing and drying the fiber to which the copper sulfide is bound.

The fibers capable of producing fabrics, knits, felts and nonwoven fabrics can be used without limit. It is possible to use vegetable fibers such as cotton fibers and hemp fibers, animal fibers, regenerated fibers such as rayon and lyocell, synthetic fibers such as polyester, polyamide, polyurethane, polyacrylic, polyvinyl alcohol, polyvinylidene chloride, polyolefin, inorganic, and the like.

In order to produce functional fibers by binding copper sulfide to the surface of a fiber, a functional group capable of coordinating with the copper atom of copper sulfide must be formed in the fiber.

Examples of the functional group include a thiol group, thiocarbonyl group, thiourea group, an azole group, an amino group, a cyano group, an amide group, and the like.

Examples of a method for introducing a functional group into a fiber include the method of grafting the monomer with a functional group such as a thiol group, thiocarbonyl group, thiourea group, an azole group, an amino group, a cyano group, an amide group to fiber, a method of treating a fiber with a silane coupling agent having the functional group, and a method of grafting a monomer having a functional group and a double bond after treating the fibers with a silane coupling agent having a double bond.

As one example, when the polyamide fiber is modified with an amino group-containing silane coupling agent or mercapto group-containing silane coupling agent, an amino group or a mercapto group can be introduced to a polyamide fiber.

In addition, when the polyamide fibers are treated with the silane coupling agent produced by reaction of azole compounds such as imidazole with 3-mercaptopropyltrimethoxysilane, azole group and a thiol group can be introduced to polyamide fiber.

As another example, when vinyltrimethoxysilane, vinyltriethoxysilane, or a mixture reacts with polyamide fiber and then acrylonitrile monomer was grafted to it, the cyano group can be introduced to polyamide fiber.

Before introducing a functional group into the fiber, the surface of fiber can be treated with a solvent such as hydrochloric acid, nitric acid, sulfuric acid, phosphoric acid, acetic acid, formic acid, citric acid, and the like to activate the surface, so that the bonding force of fiber and the compound with a functional group can be improved.

In addition, through the low-temperature plasma treatment, a polar group such as a hydroxyl group, a carbonyl group, and the like may be introduced to the surface of fiber, and the polar group may form chemical bonds with a compound having a functional group.

Since acrylic fiber contains cyano group, copper sulfide can be coordinated without the introduction of functional group.

The fiber into which the functional group is introduced is dipped in the functional copper sulfide composition, and copper sulfide can be coordinated to the surface of fiber.

The content of the fiber and the functional copper sulfide composition is preferably 10 to 80 parts by weight of a composition based on 100 parts by weight of fiber.

The bath ratio of the aqueous solution containing the fiber and the composition can be adjusted from 1:1 to 50.

The fibers are immersed in a composition having a pH of 2 to 6 and a temperature of 30 to 90° C. for 1 to 10 hours, and then it is preferable to carry out the reaction.

Coordination is carried out at 30 to 40° C. for 1 to 3 hours, at 45 to 55° C. for 1 to 5 hours and at 60 to 90° C. for 30 minutes to 1 hour. When performing coordination at high temperature, copper sulfide is not uniformly adsorbed on the fiber and the color can change. After sufficient preheating at low temperature, the temperature is increased stepwise to obtain uniform adsorption of copper sulfide to fiber.

After the coordination step, it is preferable to undergo washing and drying steps. Preferably, the fibers are washed several times with water at room temperature, and then are washed with hot water of 30 to 80° C. to remove unreacted materials, and can be dried by dehydration and emulsification.

The present invention also relates to a functional fiber which is produced by treating one or more fibers selected from a plant fiber, an animal fiber, a synthetic fiber and a recycle fiber with the functional copper sulfide composition, wherein the surface of the fiber is coated with at least one functional group selected from a thiol group, thiocarbonyl group, thiourea group, azol group, an amino group, a cyano group and an amide group, a copper sulfide and a metal sulfide are coordinately bonded to the functional group, the functional group is 1 to 10% by weight based on the total fiber weight, the copper sulfide is 1 to 15% by weight based on the total fiber weight, and the metal sulfide is 0.1 to 5% by weight based on the total fiber weight.

The functional group is preferably 1 to 10% by weight based on the total fiber weight. If the content of the functional group is less than 1% by weight, copper sulfide and metal sulfide cannot be efficiently combined to the surface of fiber. If the content of the functional group exceeds 10% by weight, excessive amount of the functional group rather interferes with the binding of copper sulfide and a powdery precipitate is formed or uneven adsorption of copper sulfide occurs.

The copper sulfide is preferably 1 to 15% by weight based on the total fiber weight. If the content of copper sulfide is less than 1% by weight, the content of copper sulfide introduced to fiber is not sufficient and it is difficult to improve conductivity and far infrared ray emissivity. If it exceeds 15% by weight, the conductivity increases but the physical properties of the fiber itself decrease and large amount of copper sulfide precipitate can be formed.

The metal sulfide is preferably 0.1 to 5% by weight based on the total fiber weight. If the content is less than 0.1% by weight, it is difficult to improve washability, washing resistance and durability of the fibers. When it exceeds 5% by weight, the conductivity of the fiber is rather reduced.

In addition, the functional fiber has the far-infrared emissivity of 0.895% or more at 37° C.; and 5 to 20 μm, the far-infrared radiation energy of $3.45 \times 10^2$ W/m$^2$·μm or more, the far-infrared emissivity after 40 times of washing of 0.892% or more, and the far-infrared radiation energy after 40 times of washing of $3.41 \times 10^2$ W/m$^2$·μm or more.

The functional fiber of the present invention shows a high far-infrared ray emissivity. Far infrared rays emitted to the human body by the fiber have the same frequency band as the natural frequency of water and protein which constitute the majority of our bodies. Far infrared rays emitted cause the increases of blood temperature and immunity, rapid fatigue recovery, blood circulation improvement, pain relief and other effects because they cause the resonance with moisture in cells and blood such as the muscle, blood vessels, lymph vessels, nerves, etc and activate it.

Further, even after 40 times of washing, the far infrared ray emissivity and the radiant energy of the functional fiber are maintained without change. Even if the functional fibers are repeatedly washed or used for a long period of time, copper sulfide and metal sulfide bound to the fiber surface are not desorbed. Therefore, the color of the fiber does not change even after repeated washing or long-term use and conductive, resistance to washing, washability, durability, moisture resistance, alkali resistance, etc. can be maintained.

The functional fiber has at least one function selected from the group consisting of antibacterial, deodorant, far-infrared radiation, wound healing, skin aging prevention, thermal storage and thermal insulation, electromagnetic shielding and static elimination.

The copper sulfide and the metal sulfide coordinated to the functional fiber of the present invention destroy cell walls and DNA of bacteria, and essentially blocks the propagation of bacteria. And it causes substances to be removed by adsorption, activates immune cells through skin peptides and copper-peptide bonds, heals wounds, prevents skin aging, absorbs and radiates heat from sunlight, re-radiates heat from the body, absorbs a wide range of electromagnetic waves, and completely removes static electricity.

In addition, the functional fiber of the present invention can be widely used in clothing, industrial and military field such as clothing, socks, gloves, bands, abdominal binder, masks, hats, bandage, scarf, bedclothes, burn pad, a hospital gown, an industrial filter and filler.

DESCRIPTION OF THE INVENTION

Hereinafter, the present invention will be described in detail with reference to Examples and Comparative Examples. The following examples are illustrated only for the purpose of carrying out the invention, but the present invention is not limited thereto.

Example 1

35% by weight of cupric sulfate pentahydrate, 5% by weight of silver nitrate, 20% by weight of ferrous sulfate, 20% by weight of sodium thiosulfate, 3% by weight of magnesium chloride, 7% by weight of trimethylene diamine, 7% by weight of sodium hydroxide and 3% by weight of citric acid were mixed to prepare a functional copper sulfide composition.

Silane coupling agent was prepared by reacting imidazole with 3-mercaptopropyltrimethoxysilane.

The polyamide fiber was impregnated in the aqueous solution containing the silane coupling agent and reacted at 50° C. for 60 minutes to prepare a surface-treated polyamide fiber.

As a result of comparing the fiber weights before and after introducing the functional group onto the surface of the fiber, the content of functional group was 2.3% by weight based on the total fiber weight.

An aqueous solution containing 60 parts by weight of the functional copper sulfide composition was prepared.

After immersing 100 parts by weight of the surface treated polyamide fibers in the aqueous solution, the reaction was carried out at 60 for 2 hours. The bath ratio of the polyamide fiber and the aqueous solution was 1:20.

The reaction-finished fibers were washed several times with room temperature and with hot water at 50° C. to remove unreacted materials, and then dried with hot air at 80° C. to obtain a functional polyamide Fiber.

As a result of comparing the fiber weights before and after reacting the functional copper sulfide composition with the functional group-introduced fiber, and performing SEM-EDS analysis of functional fiber, the content of copper sulfide was 11.5% by weight based on the total fiber weight and the content of silver sulfide was 1.8% by weight.

Example 2

35% by weight of cupric sulfate pentahydrate, 5% by weight of silver nitrate, 20% by weight of ferrous sulfate, 22.5% by weight of sodium thiosulfate, 0.5% by weight of magnesium chloride, 7% by weight of trimethylene diamine, 7% by weight of sodium hydroxide and 3% by weight of citric acid were mixed to prepare a functional copper sulfide composition.

The same procedures as in Example 1 were carried out except that above functional copper sulfide composition was used.

The content of copper sulfide was 9.8% by weight based on the total fiber weight, and the content of silver sulfide was 1.5% by weight.

Example 3

35% by weight of cupric sulfate pentahydrate, 5% by weight of silver nitrate, 20% by weight of ferrous sulfate, 17% by weight of sodium thiosulfate, 10% by weight of magnesium chloride, 5% by weight of trimethylene diamine, 5% by weight of sodium hydroxide and 3% by weight of citric acid were mixed to prepare a functional copper sulfide composition.

The same procedures as in Example 1 were carried out except that above functional copper sulfide composition was used.

The content of copper sulfide was 9.1% by weight based on the total fiber weight, and the content of silver sulfide was 1.3% by weight.

Comparative Example 1

The same procedures as in Example 1 were carried out except that silver nitrate was not used.

35% by weight of cupric sulfate pentahydrate, 22.5% by weight of ferrous sulfate, 22.5% by weight of sodium thiosulfate, 3% by weight of magnesium chloride, 7% by weight of trimethylene diamine, 7% by weight of sodium hydroxide and 3% by weight of citric acid were mixed to prepare a functional copper sulfide composition.

The content of copper sulfide was 7.9% by weight based on the total fiber weight Comparative Example 2

The same procedures as in Example 1 were carried out except that magnesium chloride was not used.

35% by weight of cupric sulfate pentahydrate, 5% by weight of silver nitrate, 22% by weight of ferrous sulfate, 21% by weight of sodium thiosulfate, 7% by weight of trimethylene diamine, 7% by weight of sodium hydroxide and 3% by weight of citric acid were mixed to prepare a functional copper sulfide composition.

The content of copper sulfide was 6.5% by weight based on the total fiber weight, and the content of silver sulfide was 0.8% by weight.

Comparative Example 3

The same procedures as in Example 1 were carried out except that trimethylene diamine was not used.

35% by weight of cupric sulfate pentahydrate, 5% by weight of silver nitrate, 23.5% by weight of ferrous sulfate, 23.5% by weight of sodium thiosulfate, 3% by weight of magnesium chloride, 7% by weight of sodium hydroxide and 3% by weight of citric acid were mixed to prepare a functional copper sulfide composition.

The content of copper sulfide was 5.5% by weight based on the total fiber weight, and the content of silver sulfide was 0.6% by weight.

Comparative Example 4

The same procedures as in Example 1 were carried out except that sodium hydroxide was not used.

35% by weight of cupric sulfate pentahydrate, 5% by weight of silver nitrate, 23.5% by weight of ferrous sulfate, 23.5% by weight of sodium thiosulfate, 3% by weight of magnesium chloride, 7% by weight of trimethylene diamine and 3% by weight of citric acid were mixed to prepare a functional copper sulfide composition.

The content of copper sulfide was 7.5% by weight based on the total fiber weight, and the content of silver sulfide was 1.1% by weight.

The specific resistance, far infrared rays emissivity, washing resistance, durability, copper sulfide content, silver sulfide content and functional group content of the polyamide fiber prepared from the above Examples and Comparative Examples were measured, and the results are shown in Table 1 and 2 below.

(Specific Resistance; Resistivity)

The specific resistance (Ω·cm) of fibers prepared according to KS K 0180 (Test Method for Electrical Resistance of Yarns, 2013), was measured.

(Far-infrared Rays Emissivity)

According to the measurement method (KFIA-FI-1005) of far infrared ray emissivity and radiation energy by infrared spectrophotometer, the light source (infrared lamp, 150 W) was irradiated to the specimen at the temperature of 37° C., the distance between the specimen and light source of 62 cm for 20 minutes, and then the far-infrared emissivity (%) and the far-infrared radiation energy (W/m$^2$·μm) at a wavelength of 5 to 20 μm were measured using FT-IR spectrometer.

(Washing Resistance)

The washing resistance test of fibers is carried out by the washing fastness test method prescribed in KS K 0430.

Specifically, 2 g of the fiber was dissolved into a stainless steel container containing 100 mℓ of a solution containing 5 g/L of a commercial detergent, and then 10 steel beads was put in container.

The container was washed in a washing fastness tester maintained at 40° C. for 30 minutes. After washing, the sample was rinsed with water and then dried to below 60° C. This washing process is repeated a predetermined number of times, and then the discoloration and the specific resistance were measured.

(Durability)

1 g of the fiber was quantitatively measured, and then was put in a thereto-hygrostat maintained at a temperature of 60° C., and a relative humidity of 95%.

The discoloration and specific resistance of the fibers were measured every 12 hour.

(Content of Copper Sulfide, Content of Silver Sulfide and Content of Imidazole Group)

The weight of the fibers before and after the introduction of the functional group onto the surface of the fiber was compared, and the content of functional groups was determined.

The functional copper sulfide composition is reacted with the fiber into which the functional group is introduced, and the weight before and after reaction was compared, and the elemental content was determined by SEM-EDS analysis of the functional fiber.

The content of copper sulfide and silver sulfide was determined by above measurement.

TABLE 1

| | color | specific resistance (Ω·cm) | After 50 washings specific resistance (Ω·cm) | Color change | Durability (color change after 48 hrs) |
|---|---|---|---|---|---|
| Example 1 | Olive green | $2.6 \times 10^{-1}$ | $4.4 \times 10^{-1}$ | No change | No change |
| Example 2 | Olive green | $7.8 \times 10^{-1}$ | $6.1 \times 10^{0}$ | No change | No change |
| Example 3 | Olive green | $8.2 \times 10^{-1}$ | $7.0 \times 10^{0}$ | No change | No change |
| Comparative Example 1 | Olive blue | $2.5 \times 10^{1}$ | $5.8 \times 10^{4}$ | Change | Change |
| Comparative Example 2 | Olive brown | $1.3 \times 10^{2}$ | $6.2 \times 10^{3}$ | Change | Change |
| Comparative Example 3 | Olive brown | $3.5 \times 10^{2}$ | $8.5 \times 10^{3}$ | Change | Change |
| Comparative Example 4 | Olive blue | $9.6 \times 10^{1}$ | $2.2 \times 10^{3}$ | Change | Change |

From the results shown in Table 1, the functional fibers of Examples 1 to 3 show low resistivity and excellent washing resistance because copper sulfide and silver sulfide are formed on the surface of the fibers. And the durability is excellent in even under the conditions of high temperature and high humidity.

In particular, in Example 1 in which the content of magnesium chloride used as a catalyst was adjusted to 3 wt %, the resistivity, the washing resistance and the durability were superior to those in Example 2 the content of magnesium chloride: 0.5% by weight) and Example 3 (magnesium chloride content: 10% by weight).

On the other hand, in Comparative Examples 1 to 4, resistivity, washability and durability were lower than those of Examples 1 to 3.

In particular, in the case of Comparative Example 1 in which silver nitrate used as a metal salt was not used, it can be seen that the washing resistance and the durability are the most inferior.

TABLE 2

| | Far-infrared rays | | After 40 washings Far-infrared | |
|---|---|---|---|---|
| | Emissivity (%) | radiation energy (W/m$^2$·μm) | rays Emissivity (%) | Far-infrared radiation energy (W/m$^2$·μm) |
| Example 1 | 0.901 | $3.49 \times 10^{2}$ | 0.899 | $3.46 \times 10^{2}$ |
| Example 2 | 0.895 | $3.45 \times 10^{2}$ | 0.892 | $3.41 \times 10^{2}$ |
| Example 3 | 0.896 | $3.47 \times 10^{2}$ | 0.894 | $3.41 \times 10^{2}$ |
| Comparative Example 1 | 0.891 | $3.42 \times 10^{2}$ | 0.879 | $3.38 \times 10^{2}$ |
| Comparative Example 2 | 0.888 | $3.40 \times 10^{2}$ | 0.881 | $3.39 \times 10^{2}$ |

TABLE 2-continued

| | After 40 washings | | | |
|---|---|---|---|---|
| | Far-infrared rays | | Far-infrared | |
| | Emissivity (%) | radiation energy (W/m$^2$ · μm) | rays Emissivity (%) | Far-infrared radiation energy (W/m$^2$ · μm) |
| Comparative Example 3 | 0.889 | 3.41 × 10$^2$ | 0.882 | 3.38 × 10$^2$ |
| Comparative Example 4 | 0.891 | 3.41 × 10$^2$ | 0.880 | 3.37 × 10$^2$ |

From the results of the above Table 2, the functional fibers of Examples 1 to 3 show excellent emissivity of far-infrared rays because copper sulfide and silver sulfide are formed on the surface of the fibers. And it can be seen that the emissivity remains constant even after repeated washing.

In particular, in Example 1 in which the content of magnesium chloride used as a catalyst was adjusted to 3 wt %, the far infrared ray emissivity was superior to those in Example 2 (content of magnesium chloride: 0.5% by weight) and Example 3 (content of magnesium chloride: 10% by weight).

On the other hand, in Comparative Examples 1 to 4, the far-infrared ray emissivity was much inferior to those in Examples 1 to 3.

INDUSTRIAL AVAILABILITY

The present invention can provide a functional fiber with excellent conductivity, washing resistance, washability, durability, moisture resistance and alkali resistance, wherein the color of the fiber is maintained even when it is washed repeatedly or used for a long time.

In addition, the present invention can provide a functional fiber which has excellent an antibacterial, deodorant, far-infrared radiation, wound healing, skin aging prevention, insulation, electromagnetic shielding and static electricity removal characteristics, and can be widely used in clothing, industrial and military field such as clothing, socks, gloves, bands, abdominal binder, masks, hats, bandage, scarf, bedclothes, burn pad, a hospital gown, an industrial filter and filler.

The invention claimed is:

1. A functional copper sulfide composition comprising a copper salt, a metal salt, a reducing agent, a sulfur compound, a catalyst, a polyamine, an alkali compound, and a pH adjusting agent,
   wherein the composition comprises 10 to 40% by weight of the copper salt, 1 to 10% by weight of the metal salt, 5 to 30% by weight of the reducing agent, 5 to 30% by weight of the sulfur compound, 1 to 5% by weight of the catalyst, 1 to 10% by weight of the polyamine, 1 to 10% by weight of the alkali compound, and 1 to 5% by weight of the pH adjusting agent;
   the copper salt is one or more selected from the group consisting of cupric sulfate salt, cupric chloride salt, cupric nitrate salt, cupric acetate salt, and cupric sulfate ammonium salt;
   the metal salt is an inorganic acid salt or an organic acid salt of a metal selected from the group consisting of gold, silver, platinum, nickel, manganese, cobalt, chromium, zinc, palladium, rhodium, ruthenium, osmium, magnesium, iron, and iridium;
   the reducing agent is one or more selected from the group consisting of metal copper, hydroxylamine, ferrous sulfate, ammonium vanadate, furfural, sodium hypophosphate, sodium hypophosphite, sodium hydrogen sulfite, glucose, and phenyl compounds;
   the sulfur compound is one or more selected from sodium sulfide, sulfur dioxide, sulfurous acid, sodium sulfite, sodium hydrogen sulfite, sodium pyrosulfite, hyposulfurous acid, sodium hydrosulfite, sodium thiosulfate, potassium thiosulfate, ammonium thiosulfate, thiourea dioxide, hydrogen sulfide, and formaldehyde sodium sulfoxylate;
   the catalyst is one or more selected from the group consisting of magnesium chloride, potassium chloride, calcium chloride, zinc acetate, ammonium chloride, ammonium sulfate, ammonium carbonate, and ammonium nitrate;
   the polyamine is one or more selected from the group consisting of methylene diamine, ethylene diamine, trimethylene diamine, tetramethylene diamine, pentamethylene diamine, hexamethylenediamine, heptamethylenediamine, diethylene triamine, triethylene tetramine, tetraethylene pentamine, and pentaethylene hexamine;
   the alkali compound is one or more selected from sodium hydroxide, potassium hydroxide, sodium carbonate, potassium carbonate, sodium hydrogen carbonate, and potassium hydrogen carbonate; and
   the pH adjusting agent is at least one selected from sulfuric acid, hydrochloric acid, phosphoric acid, nitric acid, citric acid, acetic acid, and salts thereof.

2. A functional fiber which is produced by treating one or more fibers selected from a plant fiber, an animal fiber, a synthetic fiber and a recycle fiber with the functional copper sulfide composition according to claim 1,
   wherein the surface of the fiber is coated with at least one functional group selected from a thiol group, thiocarbonyl group, thiourea group, azol group, an amino group, a cyano group and an amide group,
   a copper sulfide and a metal sulfide are coordinately bonded to the functional group,
   the functional group is 1 to 10% by weight based on the total fiber weight,
   the copper sulfide is 1 to 15% by weight based on the total fiber weight, and
   the metal sulfide is 0.1 to 5% by weight based on the total fiber weight,
   wherein the functional fiber has the far-infrared emissivity of 0.895% or more at 37° C. and 5 to 20 μm, the far-infrared radiation energy of 3.45×10$^2$ W/m$^2$·μm or more, the far-infrared emissivity after 40 times of washing of 0.892% or more, and the far-infrared radiation energy after 40 times of washing of 3.41×10$^2$ W/m$^2$·μm or more.

3. The functional fiber according to claim 2,
   wherein the functional fiber has at least one function selected from the group consisting of antibacterial, deodorant, far-infrared radiation, wound healing, skin aging prevention, thermal storage and thermal insulation, electromagnetic shielding and static elimination.

4. A molded article comprising the functional fiber according to claim 2,
   wherein the molded article includes clothing, socks, gloves, bands, abdominal binder, masks, hats, bandage, scarf, bedclothes, burn pad, a hospital gown, or an industrial filter.

* * * * *